(12) United States Patent
Arnold et al.

(10) Patent No.: US 8,198,896 B2
(45) Date of Patent: Jun. 12, 2012

(54) LOCAL COIL FACILITY FOR MAGNETIC RESONANCE TOMOGRAPHY APPARATUS

(75) Inventors: Thomas Arnold, Nürnberg (DE);
Yvonne Candidus, Tuchenbach (DE);
Thomas Kundner, Buckenhof (DE);
Ralf Ladebeck, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 168 days.

(21) Appl. No.: 12/585,311

(22) Filed: Sep. 11, 2009

(65) Prior Publication Data

US 2010/0066373 A1    Mar. 18, 2010

(30) Foreign Application Priority Data

Sep. 12, 2008 (DE) .................... 10 2008 046 974

(51) Int. Cl.
*G01V 3/00* (2006.01)
(52) U.S. Cl. .................... 324/318; 324/322
(58) Field of Classification Search .............. 324/318, 324/322, 300
See application file for complete search history.

(56) References Cited

U.S. PATENT DOCUMENTS

| 5,296,813 A * | 3/1994 | Holmes et al. ............... 324/322 |
| 5,477,146 A * | 12/1995 | Jones ........................... 324/318 |
| 5,594,339 A | 1/1997 | Henderson et al. |
| 6,577,888 B1 * | 6/2003 | Chan et al. .................. 600/422 |
| 7,282,915 B2 * | 10/2007 | Giaquinto et al. ............ 324/318 |
| 7,705,794 B2 * | 4/2010 | Shimura ....................... 343/713 |
| 2008/0088309 A1 | 4/2008 | Eberler et al. |
| 2008/0100297 A1 | 5/2008 | Ishii et al. |

FOREIGN PATENT DOCUMENTS

| DE | 69624630 T2 | 7/2003 |
| DE | 102006046287 A1 | 4/2008 |
| WO | WO 2005124380 A2 | 12/2005 |

* cited by examiner

*Primary Examiner* — Louis Arana

(74) *Attorney, Agent, or Firm* — Harness, Dickey & Pierce, P.L.C.

(57) ABSTRACT

A local coil facility is disclosed for a magnetic resonance tomography apparatus for examining an examination object. In at least one embodiment, the local coil facility includes at least one electronic processing system, a high frequency antenna, and an antenna housing to cover the high-frequency antenna and the at least one electronic processing system, the antenna housing having at least one wall close to the object and at least one wall away from the object. To reduce or even minimize the attenuation of PET radiation in a combined MR/PET device and thus in particular to ensure a better signal to noise ratio for the PET measurement, it is proposed according to at least one embodiment of the invention that the surfaces of the wall away from the object are essentially tangential to the examination object.

20 Claims, 4 Drawing Sheets

LOCAL COIL FACILITY FOR MAGNETIC RESONANCE TOMOGRAPHY APPARATUS

PRIORITY STATEMENT

The present application hereby claims priority under 35 U.S.C. §119 on German patent application number DE 10 2008 046 974.2 filed Sep. 12, 2008, the entire contents of which are hereby incorporated herein by reference.

FIELD

At least one embodiment of the invention generally relates to a local coil facility for magnetic resonance tomography apparatuses, and in particular to local coils as MR receive coils for the acquisition of MR signals in a combined PET/MR device.

BACKGROUND

Magnetic resonance tomography (MR or MRT) is an imaging method for displaying tissue in the human or animal body and is based on the principle of nuclear magnetic resonance. Atomic cores in the examination chamber can be stimulated in an applied external magnetic field with electromagnetic radiation in the high-frequency range and emit this radiation shortly afterwards. This HF radiation is detected using a local coil, which can also be used to generate the stimulating radiation.

The local coils are disposed as close to the body of the patient as possible, to increase the signal to noise ratio (SNR) of the high-frequency measurement during MR acquisition. Generally the local coils can be designed specifically for different body regions. There are therefore body coils, head coils, spine coils and others. These specific local coils are tailored as closely as possible to the anatomical shape of the body region examined in each instance.

A further medical imaging method is positron emission tomography (PET). As a nuclear medicine method PET is particularly suitable for displaying biochemical processes in the body. A radionuclide is administered to the patient, which is then distributed in the body, thereby emitting radioactive radiation in the form of positrons. The two gamma-quanta emitted in the opposite direction as the positrons decay are detected by detectors. The detectors are generally disposed in an annular manner around the body.

Since the local coils for detecting the high-frequency signals are disposed close to the body during MR acquisition, with a combination of magnetic resonance measurements (MR) and positron emission tomography (PET) they may be in the beam path of the positron annihilation radiation from the PET acquisition and may therefore disrupt the sensitivity of its detection.

Local coils for MR measurements in particular in a combined MR/PET system are known for example in the form of the field generation unit in DE 10 2006 046 287 A1. With this field generation unit the HF antenna arrangement has a first part, which is integrated in a fixed manner in the examination tunnel, so that it is disposed below the inserted patient support, and a second part, which can be positioned on the patient support and can be moved in and out of the examination tunnel with this, the second part being embodied as rigid in form and having a hollow cross section, which is tailored to the object to be examined.

With this prior art the second part comprises local coils, which are disposed above the body or head of the patient and are therefore located between the body and a PET detector facility. However in some circumstances these local coils therefore obstruct the radiation generated by positron annihilation with PET. In other words the signals for PET imaging are partially attenuated by the local coils for MR acquisition and the PET result is therefore falsified. Unfavorable beam penetration through components, for example with vertical plastic housing walls, can even result in complete extinction of the PET radiation.

Attempts are made in different ways with the prior art to correct the partial attenuation of the PET beams in the PET measurement result.

With older PET devices the attenuation of PET radiation by the components in the examination chamber is measured by way of a rotating transmission source.

With a combination of PET and computed tomography (CT) the attenuation of the PET beams is measured directly with the CT device and stored in a so-called attenuation map (µ map). To correct the PET radiation in respect of attenuation by components in the examination chamber, this attenuation map (µ map) is used when reconstructing the PET images. No high-frequency antennas are used in the examination chamber with such devices. However such high-frequency antennas are required for the PET/MR combination, so in the MR and PET combination a transmission measurement involves additional outlay. The attenuation map is therefore set out and stored in a dedicated device. The attenuation map is then used as a function of measurement position in the correction of the measurement result.

SUMMARY

In at least one embodiment of the invention the attenuation of PET radiation in a combined MR/PET device is reduced or even minimized, thereby ensuring a better signal to noise ratio in particular for PET measurement.

At least one embodiment is directed to a local coil facility for a magnetic resonance tomography apparatus.

At least one embodiment of the invention is based on the one hand on reducing the wall thicknesses of the hard plastic housings as much as possible and on the other hand on tailoring hard contours in the geometry so that they are always located optimally in the PET beam path. To this end the housings are embodied where possible with a spherical surface. This means that the radiation always penetrates the housing wall orthogonally, in other words on the shortest possible path. This reduces the attenuation of the PET radiation as much as possible.

The inventive local coil facility for a magnetic resonance tomography apparatus for examining an examination object with an antenna housing to cover a high-frequency antenna and at least one electronic processing system, the antenna housing having at least one wall close to the object and at least one wall away from the object, includes, in at least one embodiment, surfaces of the wall away from the object which are essentially tangential to the examination object.

In example embodiments of the invention, the local coil facility has as a further feature or—if technically possible and expedient—as further features, that

- the wall away from the object comprises at least one electronic system cover, having a rounded cross-sectional shape;
- the wall close to the object and/or away from the object is/are made of a polymer foam;
- the wall thickness of the wall close to the object and/or away from the object is no more than 3 mm, in particular no more than 1 mm.

One advantage of at least one embodiment of the invention is that with the new shape there are no sharp edges and the like in the examination chamber and using a particularly soft and flexible material as a cover for the antenna coils significantly reduces the risk of injury to the patient.

The local coil facility can in particular be spatially rigid, i.e. not flexible or not pliable, for example by using rigid materials for the antenna housing, e.g. made of hard plastic material. It is thus possible to embody a head coil for example in a rigid manner.

BRIEF DESCRIPTION OF THE DRAWINGS

Further features and advantages of the invention will emerge from the description which follows example embodiments, in which reference is made to the accompanying drawing.

The drawing is not to scale. Identical elements and elements with identical action are shown with the same reference characters.

DETAILED DESCRIPTION OF THE EXAMPLE EMBODIMENTS

Figure 1:
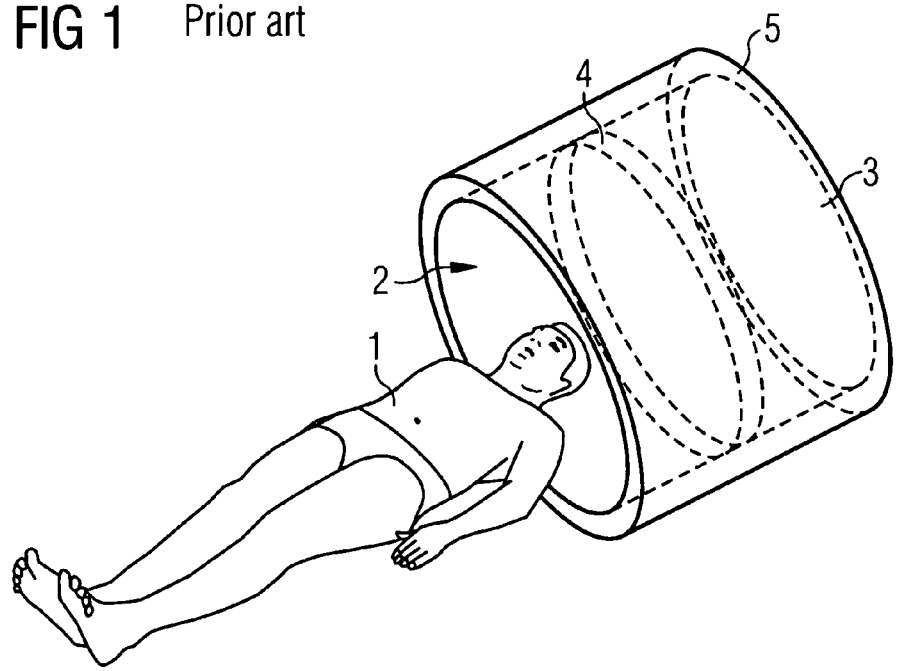
FIG. 1 shows a schematic perspective diagram of the basic structure of a combined positron emission/magnetic resonance tomography apparatus according to the prior art.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

As shown in FIG. 1, with combined PET and MRT an examination object 1 is placed in an examination chamber 2. This examination chamber 2 is enclosed by a PET apparatus 3 with a detector facility 4. The detector facility 4 is generally an arrangement of scintillation crystals (not shown), disposed in an annular manner around the examination chamber 2. In the scintillation crystals photons with an energy of 511 keV (positron annihilation radiation) are converted to light quanta, which are then in turn conducted to photodetectors (not shown), preferably by way of optical waveguides (not shown), which generate electrical output signals as a function of the number of light quanta.

To improve the local resolution of the examination at the examination object 1, the PET apparatus is enclosed by an MRT apparatus 5. As well as a basic field magnet 6 this essentially comprises a gradient coil 7 and high-frequency antennas. These elements are described below with reference to FIG. 2.

Figure 2:
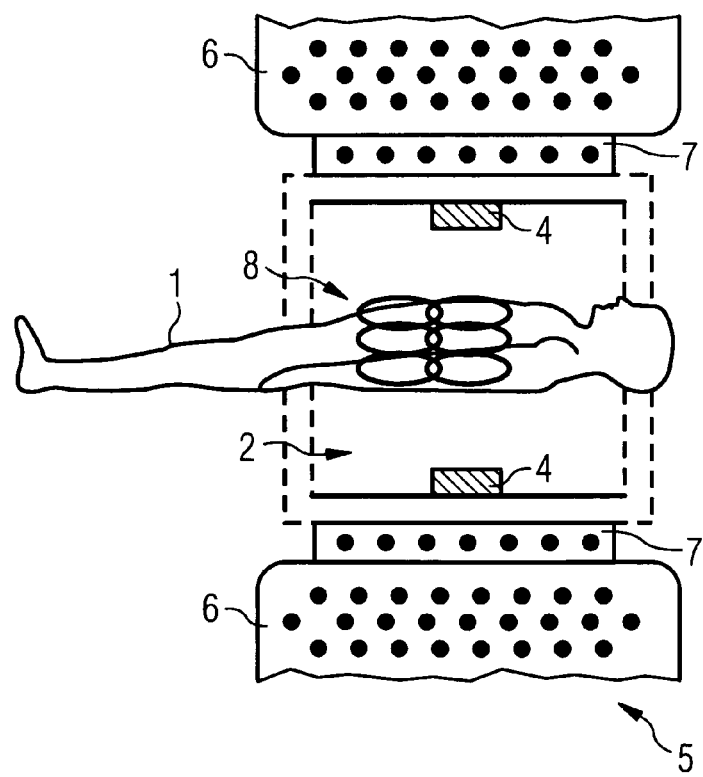
FIG. 2 shows a schematic cross section of the basic structure according to FIG. 1 with further detail.

FIG. 2 shows such a structure with further details in cross section. The examination object 1 is partially present within the examination chamber 2. The coil 6 for generating a basic magnetic field is disposed in its entirety outside around the examination chamber 2. The magnetic field induced by coil 6 in the examination chamber 2 has an axis, which corresponds to the main axis of the examination object 2 in the image plane.

Within the coil 6 a further coil is disposed in the form of the gradient coil 7, which is used to generate a gradient field in the examination chamber 2. The gradient coil 7 is wedged or bolted in the basic magnetic field coil 6, so that the two coils 6 and 7 are permanently connected to one another.

A high-frequency antenna facility (not shown) which is part of the MRT apparatus is used to radiate a high-frequency electromagnetic field into the examination chamber 2.

The high-frequency radiation emitted from the examination chamber 2 due to the high-frequency radiation being radiated in is detected with an antenna, which is an integrated part of a local coil facility 8, which is disposed as close as possible to the body of the patient 1.

Figure 3:
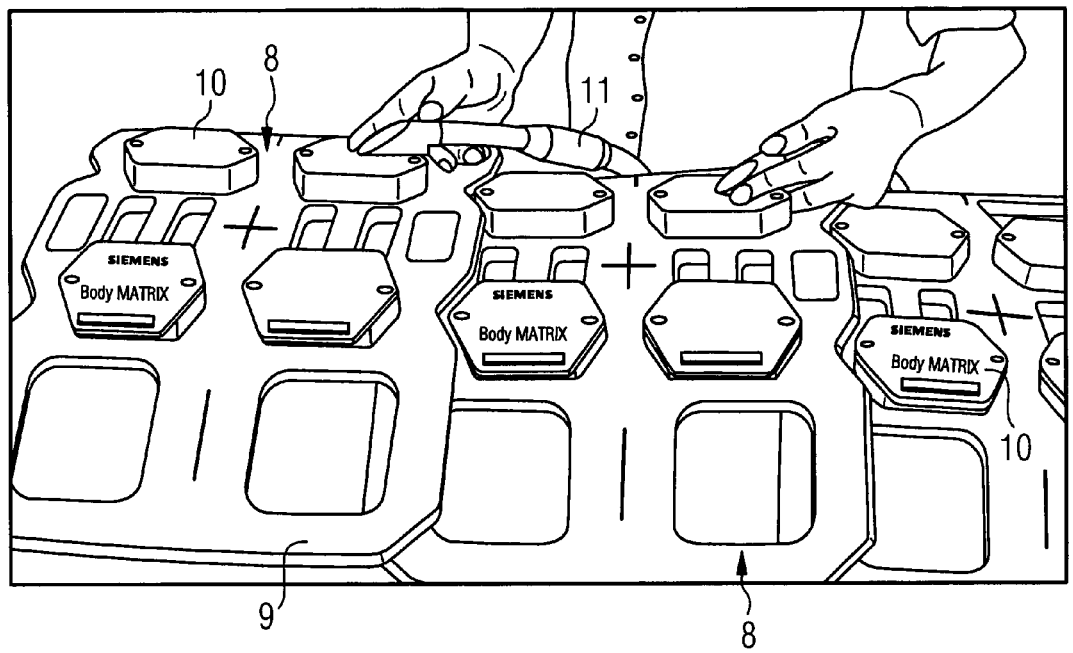
FIG. 3 shows a perspective view of an embodiment of the inventive local coil facility.

A perspective diagram of an arrangement of local coils 8 is shown in FIG. 3. The local coils 8 comprise a high-frequency antenna 9, which is cast into a plastic housing. The plastic housing here is generally made of a hard plastic material, while in contrast the body coils in contact with the body are preferably made of a polymer foam. The housing is described below with reference to FIGS. 5 and 6. The signals of the high-frequency antenna 9 are amplified in an electronic processing system 10 and conditioned to such an extent that they can be displayed visually and stored in a remote evaluation unit (not shown). The unit comprising high-frequency antenna 9 and electronic processing system 10 is connected to the remote evaluation unit (not shown) by way of a supply line 11 for this purpose.

Figure 4:
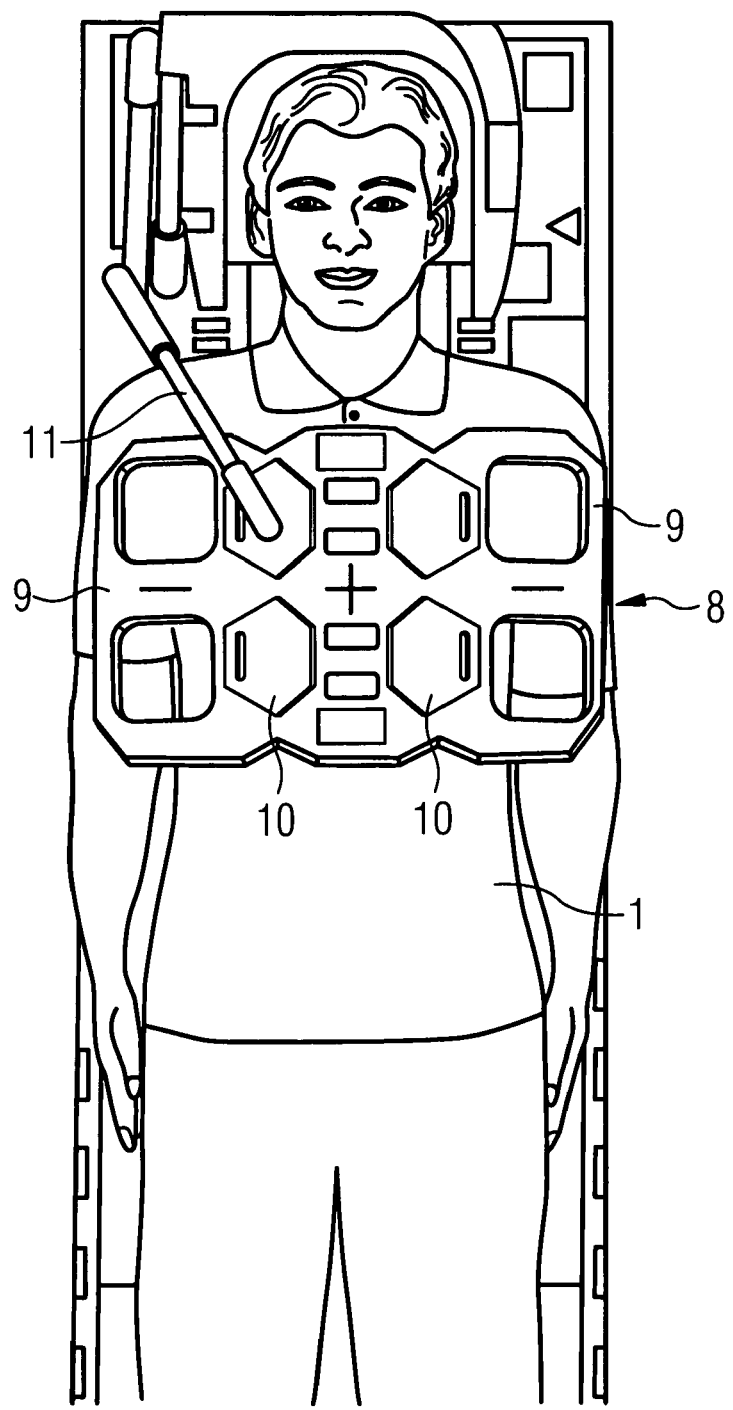
FIG. 4 shows an example application of the inventive local coil facility.

Application of the arrangement of local coils 8 in practice is shown in FIG. 4. A local coil 8 is applied directly to the patient or examination object 1 so that the high-frequency antenna 9 is as close as possible to the body of the patient and the signal to noise ratio is thus optimized.

Figure 5:
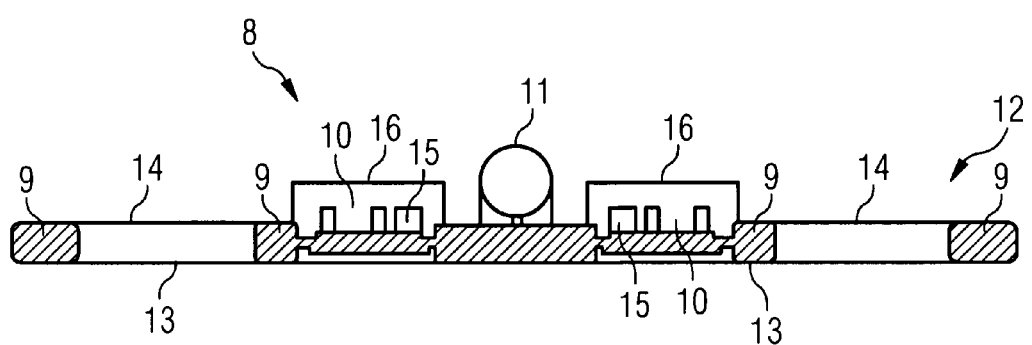
FIG. 5 shows a local coil facility according to the prior art in cross section.

FIG. 5 shows a schematic cross section through a local coil 8 with an antenna housing 12, in which the high-frequency antenna 9 is located, and a number of electronic units 10. The antenna housing 12 encloses the high-frequency antenna 9 and the electronic processing system 10 in a central segment of the local coil 8. The supply line 11 can also be connected in the central segment of the local coil 8. However this can also be connected at another point on the local coil 8, depending on the respective spatial conditions in the examination chamber.

The antenna housing 12 has a wall 13 close to the object and a wall 14 away from the object. The wall 13 close to the object allows the local coil 8 to rest directly on the examination object 1. The wall 13 close to the object must therefore satisfy the necessary medical requirements relating to breaking strength, skin compatibility, rigidity, etc. The wall 14 away from the object comprises not only the cover for the actual high-frequency antenna 9 but also a cover 16 for the electronic processing system 10. The electronic processing system 10 is made up of structural elements 15, which can be constructed discretely or can be present in the form of an integrated circuit.

As shown in FIG. 5, the wall 14 of the antenna housing 12 away from the object has vertical wall segments, in particular in the region of the cover of the electronic processing system 10. To the knowledge of the inventor these vertical wall segments or edge segments in particular are responsible for radiation in the region of 511 keV being diffused in the housing 12 and the signal thus being attenuated. This link is shown in FIG. 7 and is described in more detail below.

Figure 6:
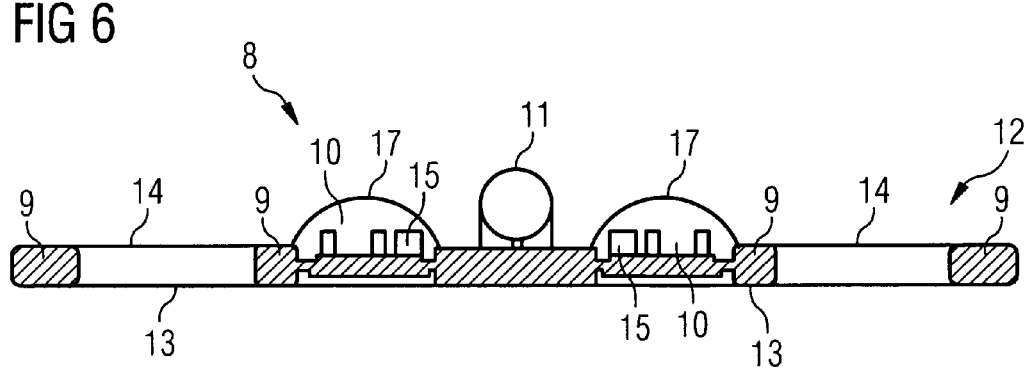
FIG. 6 shows an embodiment of the inventive local coil facility in cross section.

According to an embodiment of the invention therefore the wall 14 of the antenna housing 12 away from the object is embodied in such a manner that vertical wall segments are avoided as far as possible or are limited to a minimum height. The local coil facility 8 with the inventive antenna housing 12 is shown in FIG. 6. According to FIG. 6 the antenna housing 12 differs from the antenna housing from the prior art described above in that the cover of the electronic processing system 10 in particular has a surface, which is essentially tangential to the examination object 1. The inventive cover of the electronic processing system 10 is identified as 17 in FIG. 6. Similarly the tangential pattern of the cover can be expressed such that the surface of the inventive cover is as perpendicular as possible to radiation, the origin of which lies within the examination object 1. It follows necessarily from this that not only does the wall away from the object have an essentially tangential surface but this preferably also applies equally to the wall close to the object, in other words this also has an essentially tangential surface. This is immediately apparent if we consider that the local coil as a whole is tailored as far as possible to the respective anatomical shape to be examined.

Figure 7:
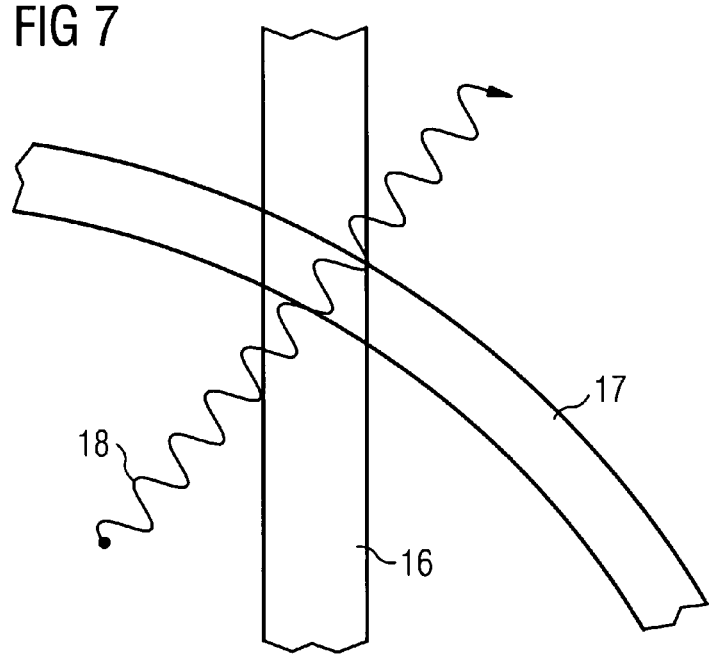
FIG. 7 shows the principle of radiation attenuation in a dense medium as a function of path length.

The reduction in the path, which the radiation from the examination object must travel through the antenna housing, is shown in FIG. 7. FIG. 7 shows the principle of radiation attenuation in a dense medium as a function of the path length as a comparison between the prior art and at least one embodiment of the invention. According to this wall segments, which do not project from the examination object perpendicular to the radial propagation of the radiation, in particular are disruptive. In FIG. 7 an electromagnetic wave 18 is shown by way of example for the radiation. Looking at the path of the radiation 18, roughly from a point below the center of the local coil 8, through a vertical wall segment in the region of the cover 16 with oblique radiation incidence, it can be seen that this is effectively longer than if the radiation 18 were to strike the wall at right angles and were to pass through a medium with greater density "only" for the actual wall thickness. The wall struck by the radiation 18 in FIG. 7 is by way of example the cover 17 of the electronic system 10.

Accordingly it is clear to the person skilled in the art that the inventive shape for the electronic system cover 17 can effectively reduce the radiation attenuation of the PET radiation due to the antenna housing 12 of the local coil 8, thereby improving the PET measurement accuracy. Optimizing the coil housing by reducing the wall thickness on the one hand and penetration on the other hand thus allows the attenuation of the PET radiation to be influenced significantly. First measurements with a coil with a wall thickness of the plastic housing of 3 mm show an overall attenuation of the PET radiation of 5.5%. A reduction in the wall thicknesses to 1 mm brings about a reduction of attenuation to only 2.9%. The wall close to or away from the object can also be made of a polymer foam. The foamed material reduces the density of the respective wall, further reducing the radiation attenuation.

The results of the first measurements with an inventive antenna housing are shown in the table below.

| Real events | Attenuation [%] |
|---|---|
| Coil 3 mm wall thickness | 5.5 |
| Coil 1 mm wall thickness | 2.9 |
| Phantom | 0 |

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A local coil facility for a magnetic resonance tomography apparatus for examining an examination object, the local coil facility comprising:
   at least one electronic processing system;
   a high frequency antenna; and
   a rigid plastic antenna housing, to cover the at least one electronic processing system and the high frequency antenna, the antenna housing including at least one wall close to the examination object and at least one wall away from the examination object, surfaces of the at least one wall away from the examination object being spherical and essentially tangential to the examination object.

2. The local coil facility as claimed in claim 1, wherein the at least one wall away from the examination object includes at least one electronic system cover having a rounded cross-sectional shape.

3. The local coil facility as claimed in claim 1, wherein at least one of the at least one wall close to the examination object and the at least one wall away from the examination object is made of a polymer foam.

4. The local coil facility as claimed in claim 1, wherein the wall thickness of at least one of the at least one wall close to the examination object and the at least one wall away from the examination object is no more than 3 mm.

5. The local coil facility as claimed in claim 1, wherein the antenna housing is embodied as rigid.

6. The local coil facility as claimed in claim 2, wherein at least one of the at least one wall close to the examination object and the at least one wall away from the examination object is made of a polymer foam.

7. The local coil facility as claimed in claim 4, wherein the wall thickness of at least one of the at least one wall close to the examination object and the at least one wall away from the examination object is no more than 1 mm.

8. The local coil facility as claimed in claim 2, wherein the wall thickness of at least one of the at least one wall close to the examination object and the at least one wall away from the examination object is no more than 3 mm.

9. The local coil facility as claimed in claim 3, wherein the wall thickness of at least one of the at least one wall close to the examination object and the at least one wall away from the examination object is no more than 3 mm.

10. The local coil facility as claimed in claim 2, wherein the antenna housing is embodied as rigid.

11. The local coil facility as claimed in claim 3, wherein the antenna housing is embodied as rigid.

12. The local coil facility as claimed in claim 4, wherein the antenna housing is embodied as rigid.

13. A magnetic resonance tomography apparatus comprising the local coil facility as claimed in claim 1.

14. A magnetic resonance tomography apparatus comprising the local coil facility as claimed in claim 2.

15. A magnetic resonance tomography apparatus comprising the local coil facility as claimed in claim 3.

16. A magnetic resonance tomography apparatus comprising the local coil facility as claimed in claim 4.

17. A combined MR/PET device comprising the local coil facility as claimed in claim 1.

18. A combined MR/PET device comprising the local coil facility as claimed in claim 2.

19. A combined MR/PET device comprising the local coil facility as claimed in claim 3.

20. A combined MR/PET device comprising the local coil facility as claimed in claim 4.

* * * * *